United States Patent [19]

Sumikama

[11] 4,000,070
[45] Dec. 28, 1976

[54] APPARATUS FOR PROTECTING A LIQUID CHROMATOGRAPHY COLUMN

[75] Inventor: Sadao Sumikama, Yokohama, Japan
[73] Assignee: Showa Denko K.K., Tokyo, Japan
[22] Filed: Mar. 24, 1976
[21] Appl. No.: 669,963

[30] Foreign Application Priority Data

Apr. 1, 1975 Japan .............................. 50-39393

[52] U.S. Cl. .......................... 210/137; 210/198 C; 210/349
[51] Int. Cl.² ...................................... B01D 15/08
[58] Field of Search ............. 210/22, 97, 137, 149, 210/349, 31 C, 198 C; 55/197, 386

[56] References Cited

UNITED STATES PATENTS 3,537,585  11/1970  Waters ........................... 210/198 C

FOREIGN PATENTS OR APPLICATIONS 1,213,694  4/1960  France ............................. 210/349

Primary Examiner—John Adee
Attorney, Agent, or Firm—Armstrong, Nikaido & Wegner

[57] ABSTRACT

An improved apparatus for protection of a liquid chromatography column is proposed. Under environmental changes in pressure and temperature, a liquid and a gas in a non-expandable container communicated with the chromatography column change their relative volume, so that the environmental changes are not transmitted to the column. To prevent the gas from entering into the column, a conduit connecting the column and the container enters into interior of the container.

11 Claims, 2 Drawing Figures

APPARATUS FOR PROTECTING A LIQUID CHROMATOGRAPHY COLUMN

This invention relates to an apparatus for protection of a liquid chromatography column, and more particularly for protection of the liquid chromatography column from the effects of environmental changes in pressure and temperature.

A liquid chromatography column is used to separate materials according to their differences in physical properties, such as adsorbability, solubility and permeability. The liquid chromatography column usually contains a liquid, which is placed in the column, and a packing of porous gel. The particles of porous gel are surrounded by the liquid. The column is usually sealed when it is not employed.

The stored column is exposed to environmental changes in temperature and pressure, with the result that the storing of the column involves considerable difficulties. When the column is exposed to temperature change, the liquid in the column expands or contracts to an extent greater than expansion or contraction of the container of the column. The extremely high internal pressure within the column, which results from a temperature increase, can cause leakage of the liquid or destruction of the container. On the other hand, due to a reduced inner pressure, which results from the temperature fall, a part of the liquid can be changed into a vapor phase or air can enter into the container due to the suction force created by the reduced pressure inside the container. A part of the packing is thus exposed to a vapor phase or air. The homogeneous gel of the packing tends to either shift or shrink when exposed to even a small vapor phase or a small amount of air. The homogenity of the packing is thus lost and experiences teach that the characteristics of the liquid chromatography column is adversely affected by an insufficiently homogeneous packing.

A system has been proposed in Japanese Published Patent Application No. 43-6840, corresponding to the United State Patent Application Serial No. 480,723, to obviate the disadvantages of a liquid chromatography column. According to the proposed system, a closed container for liquid connected to the column is constructed defining an expandable fluid tight chamber, such as an expandable bellow. The chamber and the column are completely filled with liquids and a conduit for connecting the liquid chromatography column with the chamber terminates at the wall of the chamber, thereby communicating the liquids in the container and column. The homogeneous packing is protected from gas or air, because the column is filled with liquid. Further, the charged liquid is free to expand or contract in accordance with the environmental changes in temperature and pressure, by virture of expansion or contraction of the expandable container, so that no air is sucked into the container or column. The proposed protection system, however, is defective in that it has a complicated and fragile structure, because the movable parts thereof require complicated adjustment to cope with the environmental changes in pressure and; further, the expandable container is relatively fragile. In addition, the complicated structure makes the protection device relatively expensive.

It is, therefore, an object of the present invention to provide a simple and strongly constructed apparatus for protection of a liquid chromatography column against environmental changes in temperature and pressure. A feature of the present invention resides in the fact that the protection of the liquid chromatography column is not based on a mechanism to move the movable parts of the protection device in accordance with the expansion or contraction of the expandable container.

In accordance with the object of the invention, there is provided an apparatus for protecting a liquid chromatography column against environmental conditions comprising:

a liquid chromatography column having a packing filled therein;

a fluid tight container;

a conduit for communicating the column and container, connected to both the column and container, and one end of the conduit terminating inside the container at almost the central position of the geometrical shape of the container;

a liquid occupying the majority of the inner space of the container, and completely filling both the column and conduit, and;

a gas filled in the remaining non-liquid occupied space of the container.

The container according to the present invention should preferably be made of such material that it essentially exhibits neither expansion nor contraction under storing conditions of the liquid chromatography column. A variety of materials, for example, glass, metal, or the like, can be used for the container. Although these materials naturally exhibit thermal expansion, their thermal expansion can be ignored because it is negligible from the point of view of the relatively large expansion of liquid or gas. The elastic expansion and contraction of these materials can also be ignored for the same reason. The container may in practice be made of elastic, expansible material. The least volume of liquid in the container is such that the end of the conduit terminating inside the container is not exposed to the gaseous phase in the container, even if the protection apparatus is upset or held in any position other than normal. The least volume of liquid should, therefore, be more than half of the inner space of the container. The liquid in the container is the same kind of liquid as contained in the column, such as, usually, chloroform, tetrahydrofuran and toluene.

The gas phase in the remaining non-liquid occupied inner space of the container may be air or a gaseous phase evaporated from the liquid in the container, or a mixture of air and the gaseous phase. In order to prevent even a slight influence of the gas on the quality of the liquid chromatography column, the air and the evaporated gas phase from the liquid should be replaced by a gas possessing low solubility in the liquid contained in the container. The gas which replaces the air and the evaporated gas phase of the liquid can be an inert gas. This inert gas includes inert gases defined in the periodic table, such as argon, or helium, and even nitrogen.

The invention is further illustrated with reference to embodiments thereof and the attached figures, in which.

Figure 1:
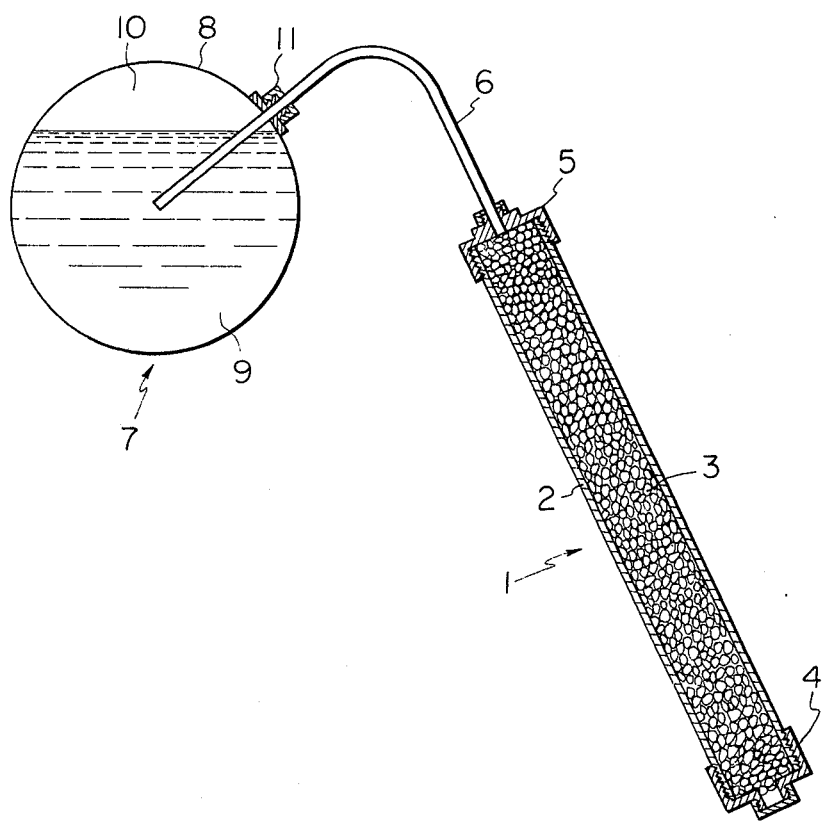
FIG. 1 is a cross sectional view of one embodiment of the protection apparatus according to the invention, wherein the relative size of spherical container with elongated tube is enlarged from the actual relative size.

Referring to FIG. 1, the protection apparatus comprises a liquid chromatography column generally indicated as 1. The column comprises an elongated tube 2, in which a homogeneous packing 3, such as homogeneous gel is filed. The gel to be used may be any known materials, such as silica gel, or a copolymer of styrene and divinylbenzene. The tube 2 is sealed at one end by a cap 4 threaded onto the tube 2. Another cap 5 provided with a through hole is threaded onto the other end of the tube 2. A thin tube 6 is liquid-tightly secured to the column through the through hole of the cap 5.

The container generally indicated as 7 consists of a spherical body 8 and a coupling 11 fitted on the body. The container, however, may be cubic, cylindrical or other polygonal. The thin conduit 6 is curved into almost a 90° angle and is gas and liquid tightly secured to the container 7. The thin conduit 6 enters the spherical body 8 through the coupling 9 and terminates at almost the center of the spherical body 8.

Figure 2:
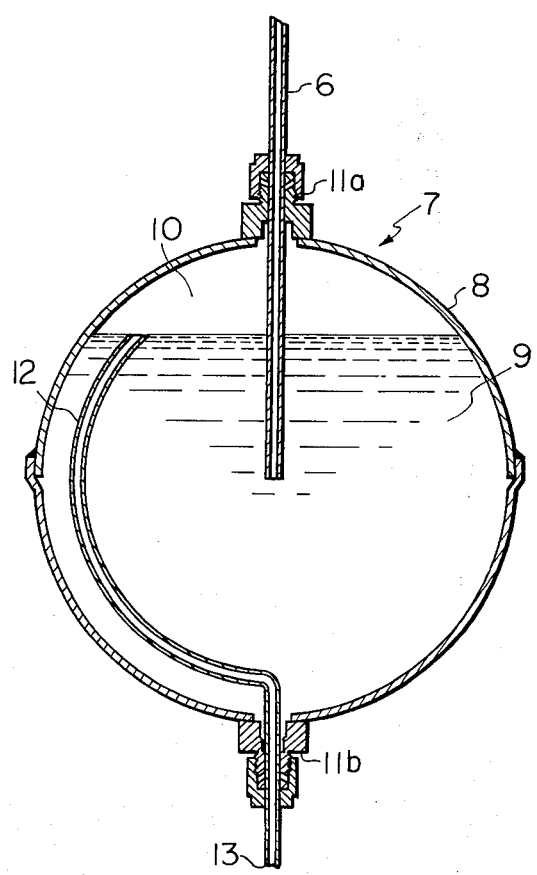
FIG. 2 is a cross sectional view of one form of the container.

Referring to FIG. 2, in which the same parts as those of the apparatus in FIG. 1 are indicated by the same reference numerals, the liquid chromatography column (not shown) is connected to the container 7 through a stainless steel conduit 6 and the coupling 11a. The container 7 has another coupling 11b fitted on the spherical body 8 directly opposite the coupling 9. A stainless steel tube 12 is gas and liquid tightly connected to the container 7 through the coupling 11 and enters the container 7. The conduit 12 runs along the inner wall of the spherical body 8 over approximately one third of the circumferential length thereof. When a gas, such as an inert gas, which replaces the air is not filled in the space 10, the conduit 12 communicates the container 7 and the atmosphere. The conduit 12, therefore, can be used before liquid is placed in the container to purge air from the space by the inert gas. The conduit 12 can also be used to remove said air with the result that gas can easily evaporate from the liquid 9 into said space. The inner space of the container 8 is occupied by approximately 70% by volume of the liquid 9 and approximately 30% by volume of the gas 10. The conduit 12 can also be used for the purpose of replacing the gas in the container 7, prior to the placing of liquid therein. The conduit 12 can, therefore, terminate at any position in the container 7. However, it is also possible to employ the conduit 12 for the described purposes subsequent to the placing of the liquid in the container. In this case, the conduit 12 must terminate within the spherical body at such a position that the end thereof protrudes into the gas phase 10 for a while when the container 8 is rotated. The liquid completely fills both the tube 2 and the conduit 6. Since the conduit 6 terminates at almost the center of the globe 8, the end of the conduit 6 does not protrude into the gas phase 10, even when the container 7 is turned upside down. In other words, the relationship between the volume of the liquid 9 and the position of the end of the conduit 6 is predetermined such that said end is always in the liquid 9.

The conduit 12 is closable at a part thereof located out of the container 7. When the conduit 12 has been used for the described purposes, the conduit 12 is cut off and sealed at the point 13, or a fluid tight plug (not shown) is inserted into the conduit 12 so that the conduit 12 does not open into the atmosphere.

The protection of the liquid chromatography column 1 is realized as follows.

The liquid in the column 1, the conduit 6 and the column 1 expands with increasing temperature. Since the liquid in the column 1 is continuous with the liquid in the container 7 through the conduit 6, the expansion of the former liquid is transmitted to the latter liquid. Although the gas contained in a vessel expands with increasing temperature, the gas 10, such as argon or helium, in the closed container is compressed by the expanding liquid 9 and thus contracts. Since, as is known, the volume change of any gas due to a pressure change is considerably greater than that of any liquid, the gas 10 in the container decreases its volume with a slight increase in the pressure of the liquid 9 in the closed container and, thus, the liquid 9 can be considered to be almost free to expand. An appreciable increase in pressure in the column 1 is, therefore, avoided by virtue of the expansion of the liquid phase 9. It is, therefore, possible to decrease the danger of liquid leakage or destruction of the column 1.

The liquid 9 contracts with decreasing environmental temperature and the gas phase 10 correspondingly increases its volume. A part of the liquid 9 thus moves through the conduit 6 into the column 1. At this time, there is no air or gas introduced into the conduit 6 and the column 1, due to the fact that a substantial part of the inner space of the container 7 is liquid 9 and, further, that the end of the conduit 6 terminates at almost the center of the globe 8.

In addition, even when the pressure outside the column changes to a considerable extent, for example, due to the shipping of the column in an unpressurized airplane, the environmental pressure change is not transmitted into the interior of the container 7. Consequently, the gas and liquid phases maintain their previous pressure, irregardless of the pressure outside. Although the material of the container, such as metal, exhibits elasticity in the general concept, the elongation and contraction of the material within the range of pressure under which the chromatography columns are stored, can be neglected. Consequently, the chromatography column can be protected from changes in environmental pressure without a complicated operation to adjust the apparatus for the pressure changes.

As will be understood from the foregoing descriptions of the invention, particularly of the embodiments thereof, the protection apparatus according to the present invention is very simple because it does not include movable parts, and, further, the gas and liquid phases change their relative volumes in accordance with environmental changes in temperature. Also, the apparatus of the invention is strongly constructed, particularly when it is made of metal. In addition, the apparatus of the invention assures highly reliable and improved protection, because the apparatus does not include mechanical parts which must be moved to cope with environmental changes. And, finally, the apparatus of the invention is less costly than the apparatus proposed in the Japanese Patent Application mentioned in the explanation of the prior art.

What I claim is:

1. An apparatus for protecting a liquid chromatography column against environmental conditions comprising:

a liquid chromatography column having a packing filled therein;

a fluid tight container;

a conduit for communicating said column and said container, connected to both said column and said container, and one end of the conduit terminating inside said container at almost the central position of the geometrical shape of said container;

a liquid occupying the majority of the inner space of said container, and completely filling both said column and conduit, and;

a gas filled in the remaining non-liquid occupied space of the container.

2. An apparatus according to claim 1, wherein said gas is either air or a gas which evaporates from said liquid, or a mixture of air and the evaporated gas.

3. An apparatus according to claim 1, wherein said gas is an inert gas.

4. An apparatus for protecting a liquid chromatography column against environmental conditions comprising:

a liquid chromatography column having a packing filled therein;

a fluid tight container which is made of material essentially exhibiting neither expansion nor contraction under said environmental conditions;

a conduit for communicating said column and said container, connected to both said column and said container, and one end of said conduit terminating inside said container at almost the central position of geometrical shape of said container;

a liquid occupying the majority of the inner space of said container, and completely filling both said column and conduit, and;

a gas filled in the remaining non-liquid occupied space of the container.

5. An apparatus according to claim 4, wherein said gas is either air or a gas which evaporates from said liquid, or a mixture of air and the evaporated gas.

6. An apparatus according to claim 4, wherein said gas is an inert gas.

7. An apparatus for protecting a liquid chromatography column against environmental conditions comprising:

a liquid chromatography column having a packing filled therein;

a fluid tight container;

a first conduit for communicating said column and said container, connected to both said column and said container, and one end of the conduit terminating inside said container at almost the central position of the geometrical shape of said container;

a liquid occupying the majority of the inner space of said container, and completely filling both said column and conduit, a second conduit connected to said container, entering said container at one end thereof and being closable at a part thereof located out of said container, and;

a gas filled in the remaining non-liquid occupied space of the container.

8. An apparatus according to claim 7, wherein said gas possesses low solubility in said liquid and is introduced through said second conduit.

9. An apparatus according to claim 8, wherein said fluid tight container is made of material essentially exhibiting neither expansion nor contraction under said environmental conditions.

10. An apparatus according to claim 8, wherein said gas is an inert gas.

11. An apparatus according to claim 10, wherein said fluid tight container is made of material essentially exhibiting neither expansion nor contraction under said environmental conditions.

* * * * *